(12) United States Patent
Puncreobutr et al.

(10) Patent No.: US 11,944,546 B2
(45) Date of Patent: Apr. 2, 2024

(54) WHOLLY PATIENT-SPECIFIC ORTHOPEDIC IMPLANTS AND IMPLANTING APPARATUSES, SYSTEM AND MANUFACTURE THEREOF

(71) Applicant: Chulalongkorn University, Bangkok (TH)

(72) Inventors: Chedtha Puncreobutr, Bangkok (TH); Boonrat Lohwongwatana, Bangkok (TH); Suriya Luenam, Bangkok (TH); Kantapat Phakdeewisetkul, Bangkok (TH); Nonphan Onsiri, Bangkok (TH); Thanawat Phetrattanarangsi, Bangkok (TH); Techawit Hirisatja, Bangkok (TH)

(73) Assignee: CHULALONGKORN UNIVERSITY (TH)

( * ) Notice: Subject to any disclaimer, the term of this patent is extended or adjusted under 35 U.S.C. 154(b) by 790 days.

(21) Appl. No.: 16/637,573

(22) PCT Filed: Aug. 8, 2018

(86) PCT No.: PCT/TH2018/000035
§ 371 (c)(1),
(2) Date: Feb. 7, 2020

(87) PCT Pub. No.: WO2019/035777
PCT Pub. Date: Feb. 21, 2019

(65) Prior Publication Data
US 2020/0253740 A1   Aug. 13, 2020

Related U.S. Application Data

(60) Provisional application No. 62/542,914, filed on Aug. 9, 2017.

(51) Int. Cl.
*G06T 19/20*   (2011.01)
*A61F 2/30*   (2006.01)
(Continued)

(52) U.S. Cl.
CPC ........ *A61F 2/30942* (2013.01); *A61F 2/4241* (2013.01); *A61F 2/4261* (2013.01); *A61B 2034/102* (2016.02); *A61B 2034/105* (2016.02); *A61B 2034/108* (2016.02); *A61F 2002/30624* (2013.01); *A61F 2002/30784* (2013.01); *A61F 2002/3092* (2013.01);
(Continued)

(58) Field of Classification Search
CPC ................................. G06T 17/10; G06T 19/20
See application file for complete search history.

(56) References Cited

U.S. PATENT DOCUMENTS

| | | | |
|---|---|---|---|
| 2012/0271613 A1* | 10/2012 | Ashby | G16H 30/20 703/11 |
| 2015/0202024 A1* | 7/2015 | Fisker | G16H 20/40 433/213 |
| 2016/0338776 A1* | 11/2016 | Jaramaz | G06T 17/10 |

* cited by examiner

*Primary Examiner* — Edward Park
(74) *Attorney, Agent, or Firm* — Parsons Behle & Latimer

(57) ABSTRACT

The present invention involves orthopedic implants of small joints in human, in particular a truly patient-specific bone implanting system comprising the implant and surgical tools fabricated by additive manufacturing techniques based on the inputs conforming to each patient's anatomy and obtainable from a wide range of existing 3-dimensional imaging and image processing technologies, which offers a substantial progress in logistics, efficiency of surgical operation, and functionality of treated bones.

19 Claims, 14 Drawing Sheets

(51) Int. Cl.
*A61F 2/42* (2006.01)
*A61B 34/10* (2016.01)
(52) U.S. Cl.
CPC ............... *A61F 2002/30948* (2013.01); *A61F 2002/4243* (2013.01); *A61F 2002/4264* (2013.01); *A61F 2002/4266* (2013.01)

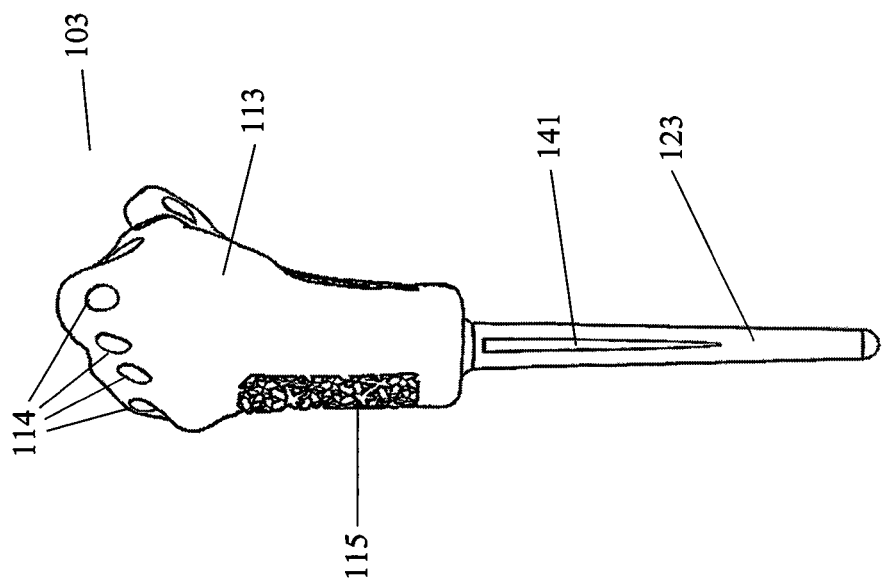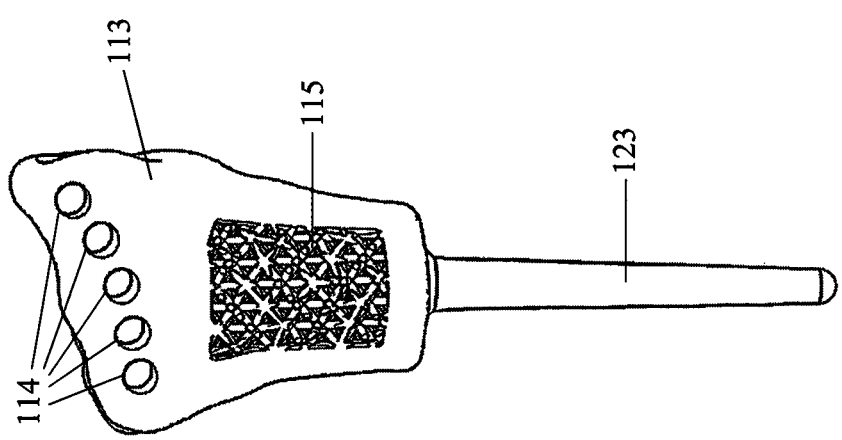

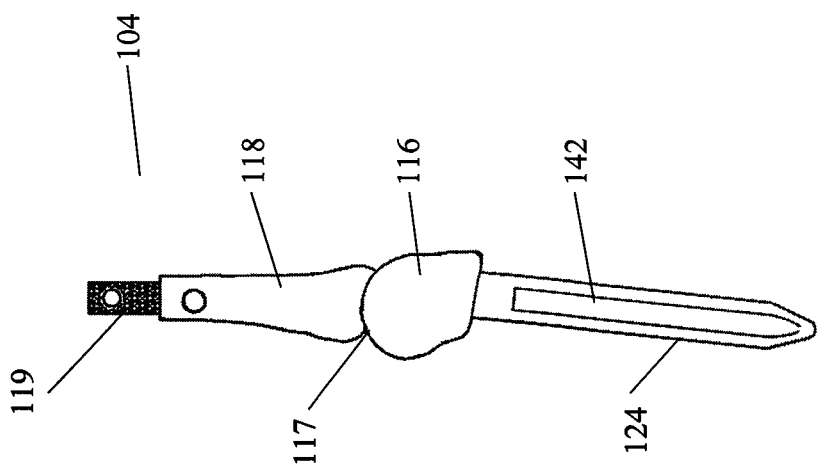
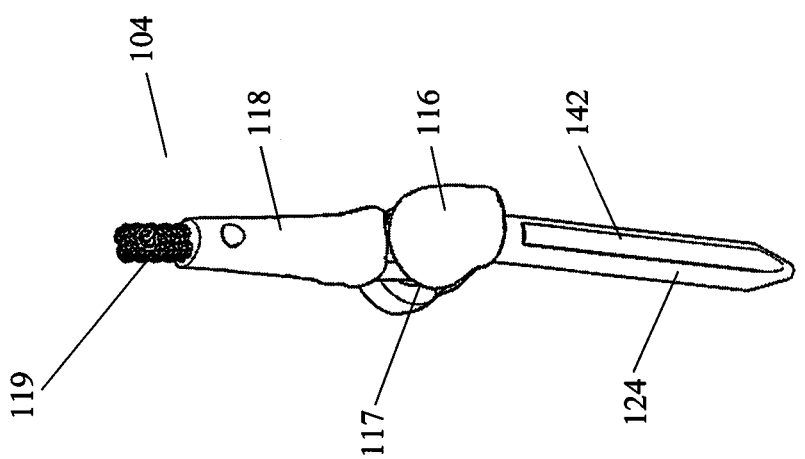

WHOLLY PATIENT-SPECIFIC ORTHOPEDIC IMPLANTS AND IMPLANTING APPARATUSES, SYSTEM AND MANUFACTURE THEREOF

TECHNICAL FIELD

The present invention relates to orthopedic implants and surgical tools for small joints in human, methods of designing patient-specific implants and additive manufacturing techniques applied to the fabrication of medically relevant articles.

BACKGROUND OF THE INVENTION

A small joint bone implant's fitness to individual patient's anatomy is strongly correlative to the efficacy of treatment of pathologies—including trauma, tumors, rheumatoid and osteoporosis—that call for bone replacement. Misfit between the shapes and dimensions of implant and those of the patient's natural bone(s) has been constantly found a major cause of limited functionality of the implanted organ, and post-treatment injuries due to, among other things, bone fatigue or wearing of intramedullary cavity into which the implant has been inserted. Even for an internationally accepted standard, a small joint bone implant is expected to maintain only a passable performance—that is, until the pain or reduced mobility necessitates a follow-up operation.

This fitting problem is not limited to the matter of size and shape: individual's each bone, including cortical and cavity parts, has distinctive angles, curvatures, dents, protrusion, and other non-uniformities, which may vary further owing to the natural configuration of neighboring bone(s) or deformation caused by the pathology. Such complexity has long aggravated the inadequacy of pre-manufactured, standardized implants (however many sizes available they are) as well as the difficulty of fabricating an implant that truly satisfies each patient's anatomical needs.

In respect of the bone operation process, surgeons in the relevant technical fields recognize the need to preserve as much of patient's natural bone as it is practical, which often conflicts with the need to remove all defective parts. Said decision-making is further constrained by the other needs to operate the patient with minimal consumption of time and damages to adjacent muscles and tissues. Usage of conventional surgical tools, e.g. a cutting guide, suffers a similar vexation: a pre-manufactured tool offers a poor fit with the patient's anatomy, resulting in a suboptimal operation speed, precision, and stability. In many cases, especially where the angle of bone resection is an important factor, a cutting error may compel the surgeon to relocate the position to be sawn off.

Prosthesis that is not sufficiently patient-specific also causes problem while it is being implanted: often the surgeon is forced to change the implant selection/combination, or manually reconfigure the implant mid-operation; worse, some would opt to scrape the intramedullary cavity—thinning the bone even further—to fit a natural bone to an inflexible implant.

Apart from being illustrative of a treatment system that is sluggish and painful, the above factors also add to the patient's slow recovery and risks of developing post-operation injuries.

Use of standardized prostheses also entails logistical costs, including inventory management and transportation. To enable the patient's access to the treatment, parties along the supply chain, in many cases the government, has to bear such costs.

U.S. Pat. No. 8,353,965 to Seitz Jr. William H and Santilli Albert N discloses a custom set of small joint orthopedic implant, a surgical tool (i.e. a rasp for cleaning the intramedullary cavity before insertion of implant), and an impact tool, all of which having corresponding dimensions. These modules are preferably fabricated by machining means. Their dimensions are approximated from the scaled 2-dimensional radiography of the patient's relevant bones. This method accurately captures only the bone head's height and width, while letting finer features (e.g. dents and curvatures) elude, affecting significantly the anatomic fitness of resulting implant. The stem of this implant is preferably projecting straight along a longitudinal axis. This arrangement disregards the curved, non-uniform outline of intramedullary cavity which is particularly conspicuous where the cavity is further from the joint, meaning the implant per this patent is good only where the receiving bone cavity is straight, for example, a position past radial tuberosity. Moreover, the dimensions of this implant are determined from a set of dimension matrices, according to which the difference between each order of size is often millimeters. The implant resulted from this approach is at best an estimate, subject to mid-operation adjustments to attain fitness for insertion.

U.S. Pat. No. 7,452,381 to Mayo Foundation for Medical Education and Research discloses a radial head replacement system (also referred to as a toolkit) which takes into account a flexible spatial relationship between the bones and prostheses. In this case, a set of screws is used to affix the head with the stem at any desired angle, and a cutting guide is capable of being slid along the axis of defective bone and adjusted for angled osteotomy. Still, the said workings have to be carried out manually mid-operation, and this system requires twice resection of the bone. This does not improve much of the speed and accuracy.

The abovementioned have demonstrated that the current state of the art is conceptually fragmented and offers neither a small-joint implant nor an implanting system that is truly patient-specific.

SUMMARY OF THE INVENTION

The present invention pertains to a single orthopedic implanting system that addresses all the aforementioned problems. Said system is integrated both vertically (i.e. from the manufacture of implant to completion of surgery) and horizontally (i.e. relevant to a wide range of raw materials, positions of the defective small joint, and natures of pathology). Enablement of the present invention is based upon the inventive concept of wholly patient-specific design of implant and surgical tools obtainable from the means of additive manufacturing.

An existing technique capable of generating a 3-dimensional image of human interior, including but not limited to CT-scan and Mill, is utilized to capture true-to-scale 3-dimensional images of relevant bone(s). This is to find reference points for the position of osteotomy, surgical tool placement, and shape of implant. Since a human's bone counterparts (e.g. left-arm's and right-arm's elbow joint) are not identical, the optimal reference points are obtainable from the images of the small joint bone subject to resection (e.g. the pathological bone). If said bone is so damaged that effective reference points cannot be located. the reference points may instead be found on the processed mirrored image of that bone's counterpart (i.e. the one not subject to resection). Because the detailed topography of the bone (dents, bumps, curvatures, etc.) is captured by this technique, the reference points are not required to be as protrusive as a tuberosity to produce the effective patient-specific fitness; an aggregate of those bits of "biometric" marks would be sufficient. It is also contemplated that images from both counterparts are used for said purposes.

The ability to utilize inconspicuous natural bone marks as reference points makes the system in accordance to the present invention applicable to small joints in any bodily positions and for a broad range of pathologies. For instance, riddance of the need to refer the positioning of cutting guide to a radial tuberosity enables a patient-specific treatment even where the radial tuberosity has decayed because of bone cancer.

Fabrication of the implant and other apparatuses in the system in accordance with the concept of this invention relies upon the abovementioned images, any existing additive manufacturing machine (i.e. a 3-D printer) and any orthopedically accepted 3-D printing materials, including titanium alloys and stainless steels. Resulting objects will be truly patient-specific, that is, providing the effective fitness to one patient alone and not to any other, and more effective fitness to that one patient than the implant and surgical tool fabricated otherwise. This better fit offers optimal functionality (e.g. mobility of the implanted joint) and minimal post-operation bone fatigue or pain.

In one embodiment, novel computer-based methods are utilized to generate the designs of small-joint implants that are personalized to a patient's individual anatomy. In one embodiment, a 3-D printed implant includes a head and a stem. Manufactured by this means, the head will feature a complex shape that fits tightly to its adjacent bone(s). In another embodiment, the stem could be made as short or long, straight or curved, smooth or uneven, as the receiving bone cavity's anatomy and pathology may require. In yet another embodiment, the spatial relationship, i.e. angle, between the head and the stem may be reproduced with fidelity to the patient's natural bone. According to another embodiment of the present invention, the stem may be grooved along its axis, or the stem's surface may be designed otherwise to aid the flow or adhesion of bone cement, which in turn facilitates the bone ingrowth.

In one embodiment, a surgical tool fabricated in accordance with the present invention can effectively interlock the cortical bone area over which it is placed. This maximizes friction between the tool and the bone to be operated upon while minimizing the contacting surface area required for supporting the guide affixation, and thus prevents more surrounding muscles and tissues from being excessively damaged and enables more speed and accuracy of the operation. This concept is applicable to a range of surgical tools, including a cutting guide, screwing guide and bone plate.

A preferable example of implanting surgery performed in accordance with the present invention involves performing the extensor digitorum communis tendon (EDC) splitting approach to open EDC and radial collateral and annular ligaments around the site of the operation. The surgeon may choose any other conventional technique that is suitable for each patient's particular case. Said operation, when performed using the implant and surgical tool fabricated in accordance with the present invention, requires minimal involvement of healthy tissues, muscles, and bones; minimal "cleaning" of the receiving bone canal; a few pieces of apparatuses; one time of bone resection and implant insertion; and no mid-operation trial-and-error or manual adjustment. In combination with the improved speed and accuracy, the patient would enjoy a quicker recovery.

The present invention also allows an operation by which (a) pre-pathologic imaging and collection of images of relevant joints is carried out in anticipation of future surgery; and/or (b) the logistical problem is overcome by separating the premises where the images are taken from where the images are stored or processed from where the implant and surgical tool is actually fabricated, and wherein the unprocessed or processed images are transferrable between these premises by known means of telecommunication or computer network.

BRIEF DESCRIPTION OF DRAWINGS

FIGS. 2A and 2B show an example of patient-specific implant for a small joint bone (distal radius) comprising a head and a stem, with holes and porous structure.

FIGS. 3A and 3B show an example of a patient-specific implant for a small joint bone (interphalangeal joint) comprising a head and two stems, with a hinged joint and porous structure at one stem.

DETAILED DESCRIPTION OF EMBODIMENTS OF THE INVENTION

Reference will now be made in detail to the various embodiments of the present invention illustrated in the accompanying drawings. Wherever possible, the same or like reference numbers will be used throughout the drawings to refer to the same or like features. It should be noted that the drawings are in a simplified form and are not drawn to precise scale.

Furthermore, the described features, advantages, and characteristics of the exemplary embodiments of the present invention may be combined in any suitable manner in one or more embodiments. One skilled in the relevant art will recognize, in light of the description herein, that the present invention can be practiced with one or more of the specific features or advantages of a particular exemplary embodiment. In other instances, additional features and advantages may be recognized in certain embodiments that may not be present in all exemplary embodiments of the present invention.

THE IMPLANT. FIG. 1 shows an implant 100 for fitting to an intramedullary cavity of a small joint bone of which an end has been resected, comprising a head 110 and a stem 120, wherein one end of the stem is attached to the head. Both the configurations of head 110 and stem 120, including an angle by which they are attached 130 could be tailored to suit each patient's specific anatomical needs. Each of this feature may be produced separately.

In one embodiment, A head 110 may have dimensions, shape, and topography corresponding to the anatomy of a small joint bone's head. Said anatomy may be based on a three-dimensional image of a small joint bone subject to resection, or a processed mirrored three-dimensional image of the bone not subject to resection. Owing to the fact that the configurations of two pieces of bone cannot be identical, even though they are limb counterparts of the same person, the best result is obtainable from an image of the small joint bone subject to resection, but the choice of referenced image will ultimately be decided by the responsible doctor. For example, if the small joint bone subject to resection is excessively deformed, the doctor may choose to reference the head to the processed mirrored image of the bone not subject to resection instead, which still gives a sufficient and effective patient-specific fit with the patient's anatomy.

Figure 5:
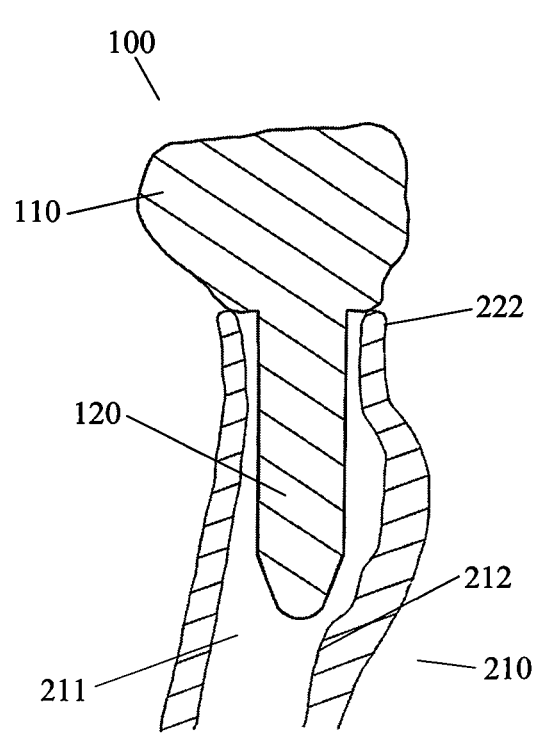
FIG. 5 shows an example of a cross-sectioned image of installed patient-specific implant for a small joint bone (radial head), the stem part (straight) being inserted into the intramedullary cavity of the resected bone.
Figure 6:
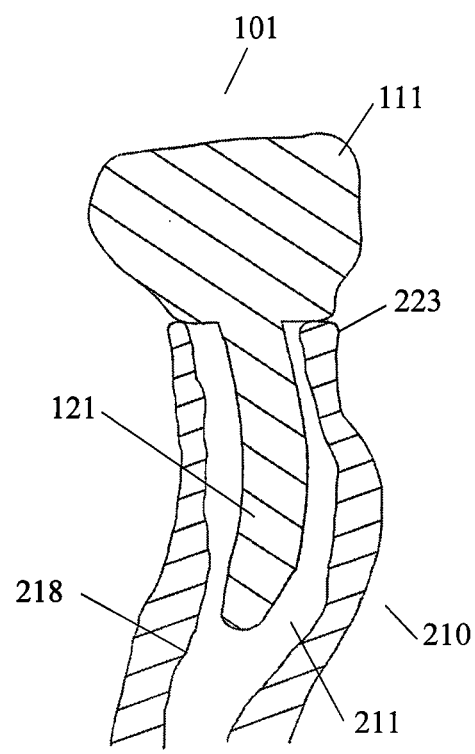
FIG. 6 shows an example of a cross-sectioned image of installed patient-specific implant for a small joint bone (radial head), the stem part (curved) being inserted into the intramedullary cavity of the resected bone.
Figure 8:
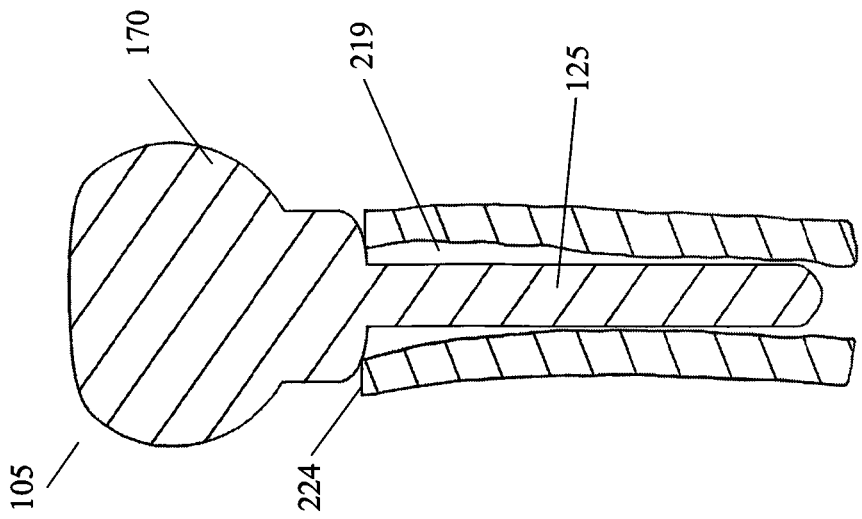
FIG. 8 shows an example of a cross-sectioned image of installed patient-specific implant for a small joint bone (ulnar head), the stem part (straight) being inserted into the intramedullary cavity of the resected bone.

In one embodiment, a stem 120 has dimensions and shape corresponding to the anatomy of the intramedullary cavity of the bone into which the stem is intended to be inserted. In an embodiment. A stem 120 is made straight, protruding from the head 110 along a longitudinal axis, as shown in FIG. 5. In another embodiment, a stem 121 is made curved, protruding from a head 111 along a curved axis, as shown in FIG. 6. Said choice will be made for purposes of fitting with the specific anatomy of patient's intramedullary cavity. In one embodiment as shown in FIGS. 5 and 6, an intramedullary cavity 211 of resected small joint bone (radial head) is provided with appropriate clearance so that the internal wall 218 is not worn by a contact against a stem 120 or 121.

Figure 1B:
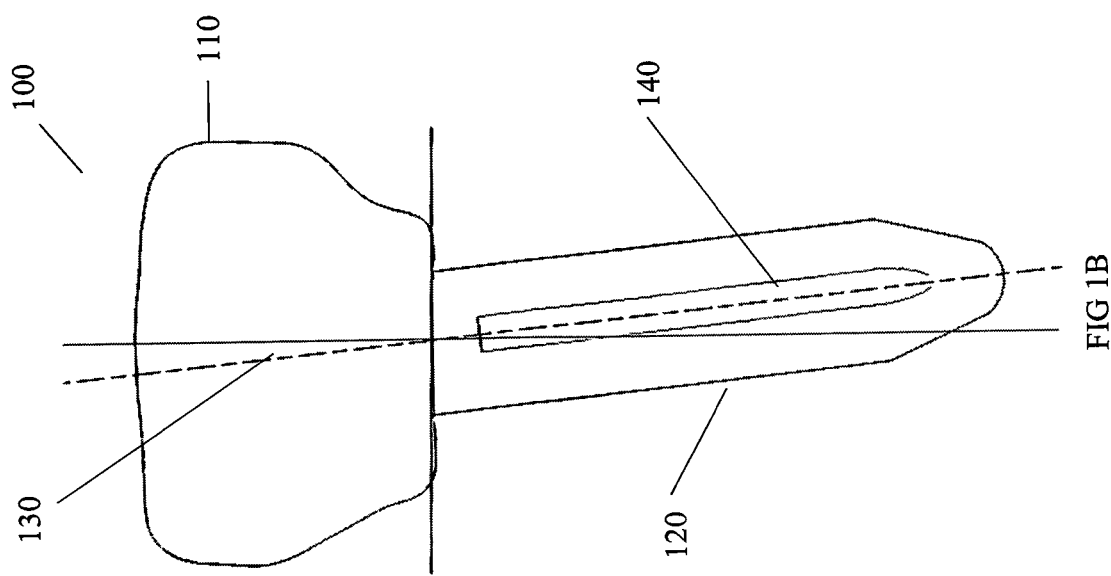
FIGS. 1A and 1B shows an example of a patient-specific implant for a small joint bone (radial head) comprising a head and a stem.
Figure 1A:
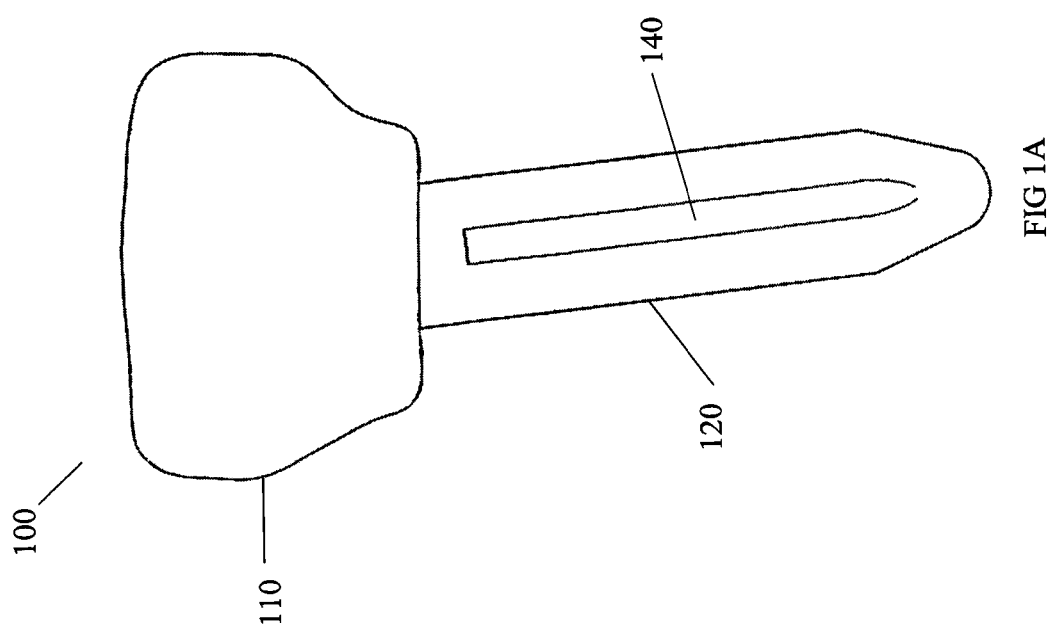
Figure 4:
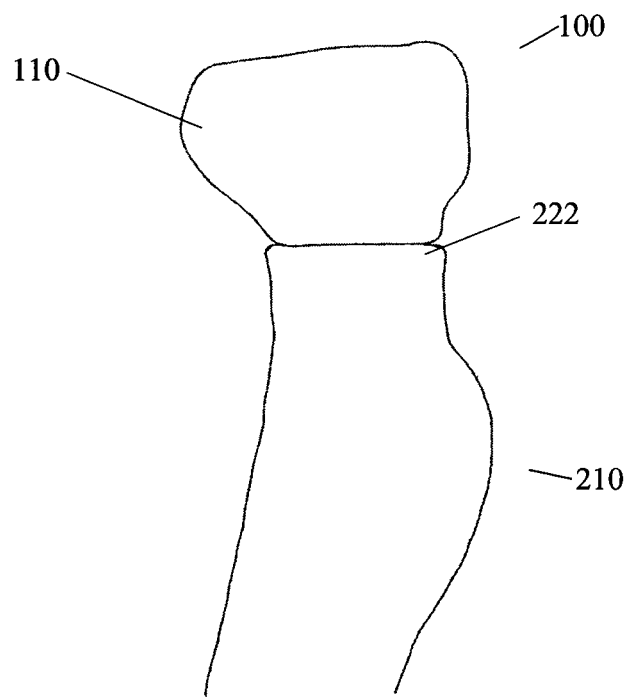
FIG. 4 shows an example of an installed patient-specific implant for a small joint bone (radial head), the stem part being inserted into the intramedullary cavity of the resected bone.

As shown in FIGS. 1A and 1B, a stem 120 may be further configured to prevent rotation or aid the flow or distribution of bone cement (not shown) in case the responsible doctor decides to prescribe so, according to the patient's needs. In one example embodiment, a stem 120 includes a fluted surface 140 along its longitudinal axis.

Figure 7:
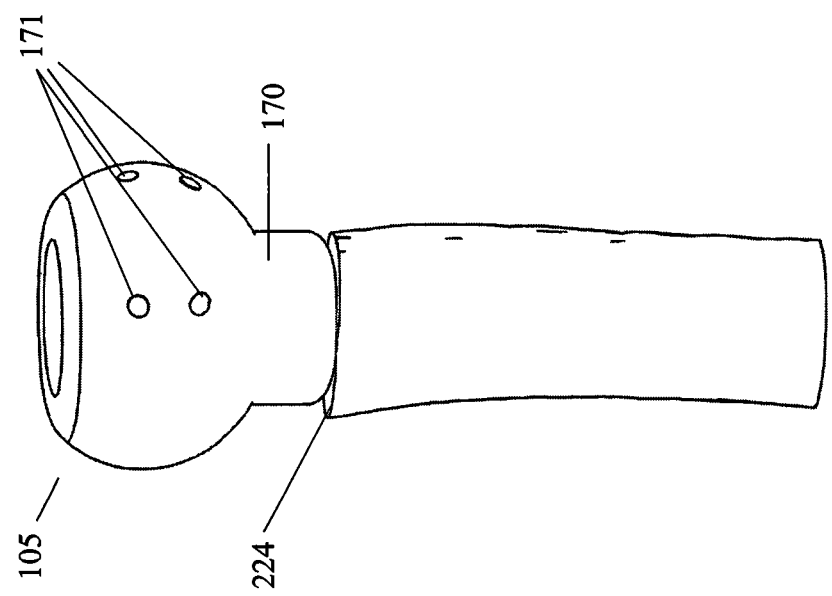
FIG. 7 shows an example of an installed patient-specific implant for a small joint bone (ulnar head) comprising a head and a stem, the stem part being inserted into the intramedullary cavity of the resected bone.
Figure 9:
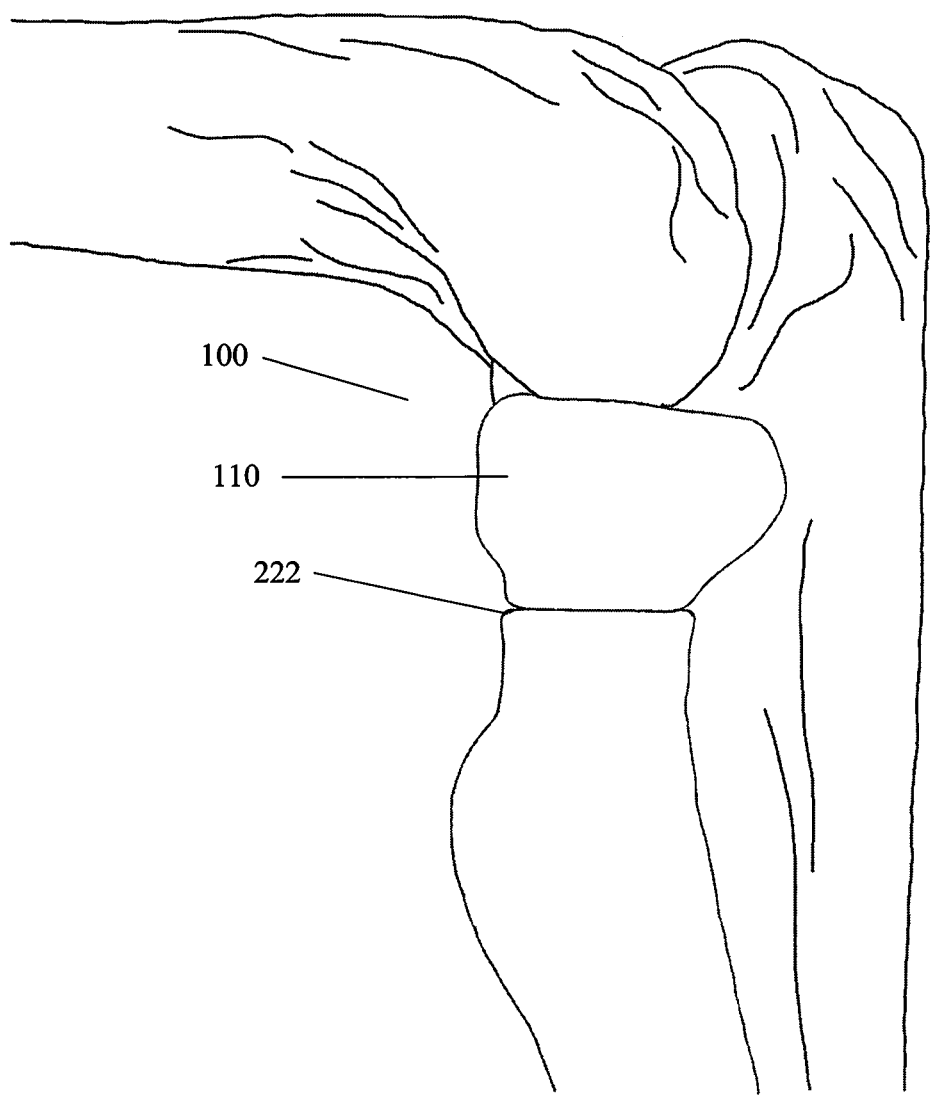
FIG. 9 shows an example of a small joint bone (radial head) implanted with a patient-specific implant, in relation to the entire small joint and neighboring bones.
Figure 10:
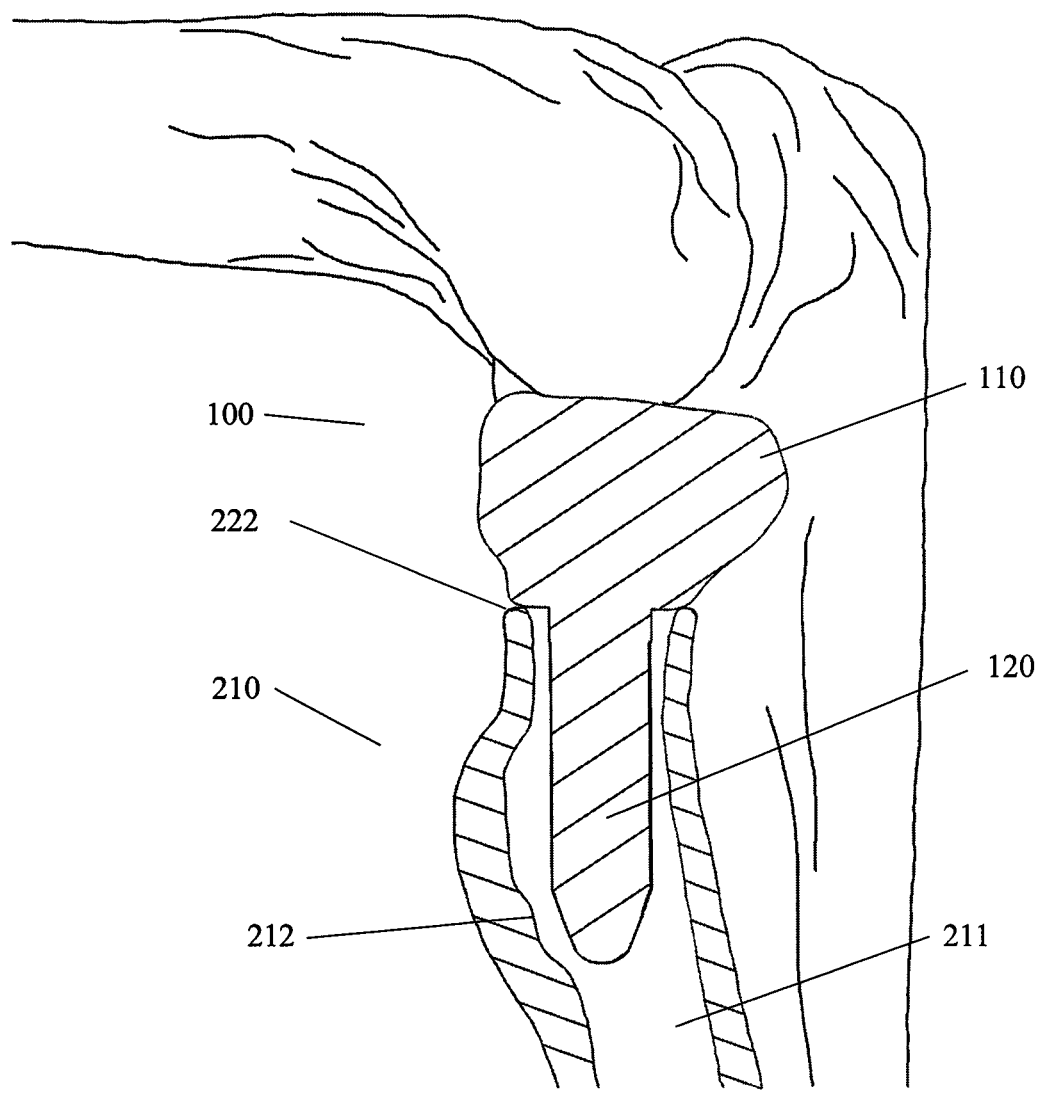
FIG. 10 shows an example of a partially cross-sectioned image of a small bone (radial head) implanted with a patient-specific implant, in relation to the entire small joint and neighboring bones.

In addition to the above embodiments, other surface or structural architectures may be applied to the implant pursuant to the means of fabrication to be described below. Example embodiments, which may be present separately or integrally, are shown in FIGS. 2A, 2B, 3A, 3B and 7. In FIGS. 2A and 2B, a head 113 has holes 114 and porous structure 115 while a stem 123 may or may not have another embodiment of fluted surface 141 to prevent unintended rotation and help the flow of bone cement (not shown). Similarly, in another embodiment as shown in FIG. 7, a head 170 has holes 171. Said holes (114 or 171) are used for temporary fixation by a wire or screw, or a plurality or combination thereof (not shown). A porous structure 115 (which may also be called a lattice structure, empty space or void) is used for osseointegration, load distribution and/or weight reduction purposes.

Further, in embodiments disclosed in FIGS. 3A and 3B, a head 116 is connected to a first stem 124 and a hinged joint 117 which is connected to a second stem 118. A first stem 124, which may or may not have a fluted surface 142 to prevent unintended rotation and help the flow of bone cement (not shown), or one or a combination of abovementioned embodiments, is intended to be inserted into a bone cavity (not shown) and so fixed with the patient's bone into which it is inserted (not shown). Either of the stems may have a porous stem tip 119 to promote osseointegration. When the installation has been completed, a first stem 124 and a porous stem tip 119 will be fixed with different pieces of bone and the hinged joint 117 will allow movements between articular surfaces of two or more parts or the head, emulating the natural hinge joint function. The foregoing embodiments, separately or integrally, may be selected by ordinarily skilled surgeon to suit each patient's case.

In one embodiment as shown in FIG. 1B, a head 110 is attached to the stem 120 at an angle 103 conforming to the three-dimensional image of the small joint bone subject to resection, or the processed mirrored three-dimensional image of the bone not subject to resection.

In any example embodiment from FIG. 1A to FIG. 10, a head (110, 111, 112, 113, 116 or 170) and a stem (120, 121, 122, 123, 124 or 125) may be made so that they are either fixedly or detachably attached to each other.

The inventors have contemplated that the concept of the present invention (i.e. the fabrication of a stem and that a stem may be detached or fabricated separately from a head) may be applied to fabricate another embodiment, which is an orthopedically compatible object for insertion into an intramedullary cavity of a small joint bone's shaft having patient-specific dimensions and shape which correspond to anatomy of said intramedullary cavity, though serving a different function from the stem. Said orthopedically compatible object may include a spacer, which is used for a temporary insertion into the bone cavity.

The concept in accordance with the present invention may as well be flexibly applied to fabricate implants or orthopedically compatible objects suitable for different small joint bones. In an exemplary embodiment shown in FIGS. 1A and 1B, the implant 100 is suitable for radial head bone; in another exemplary embodiment shown in FIGS. 2A and 2B, the implant 103 is suitable for distal radius bone; in another exemplary embodiment shown in FIGS. 3A and 3B, the implant 104 is suitable for interphalangeal joint bone; in another exemplary embodiment shown in FIG. 7, the implant 105 is suitable for ulnar head bone. It is further contemplated the concept of the present invention may be applied as effectively to obtain implants for small joint bones located at a shoulder, elbow, wrist, hand, fingers, ankle, foot, or toes.

Figure 11B:
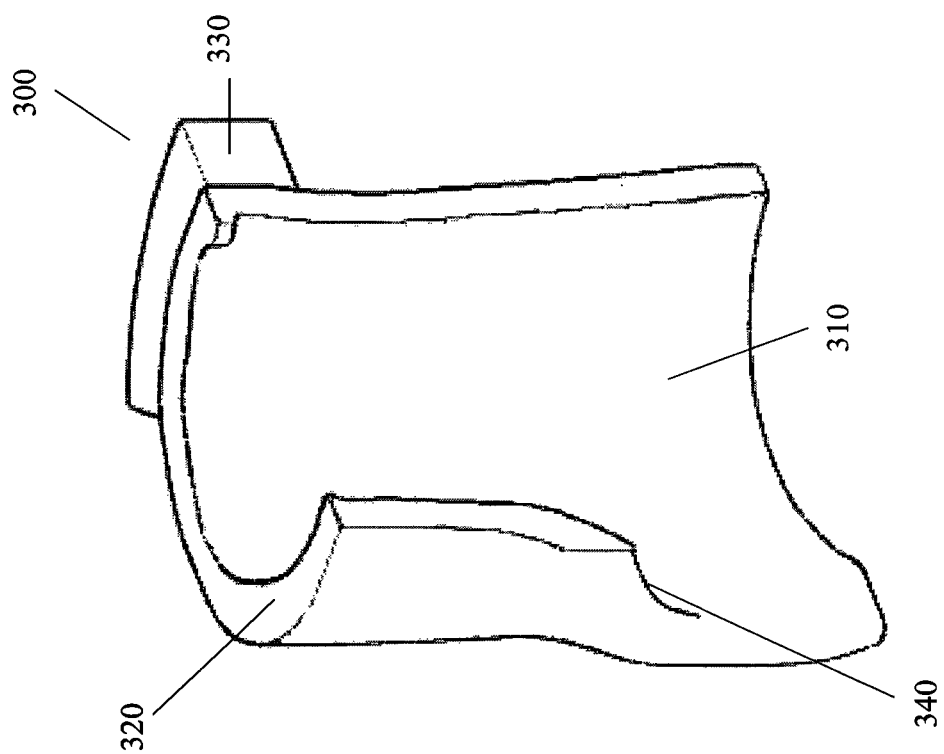
FIGS. 11A and 11B show an example of a patient-specific cutting guide for radial head, an example of surgical tools fabricated in accordance with the present invention.
Figure 11A:
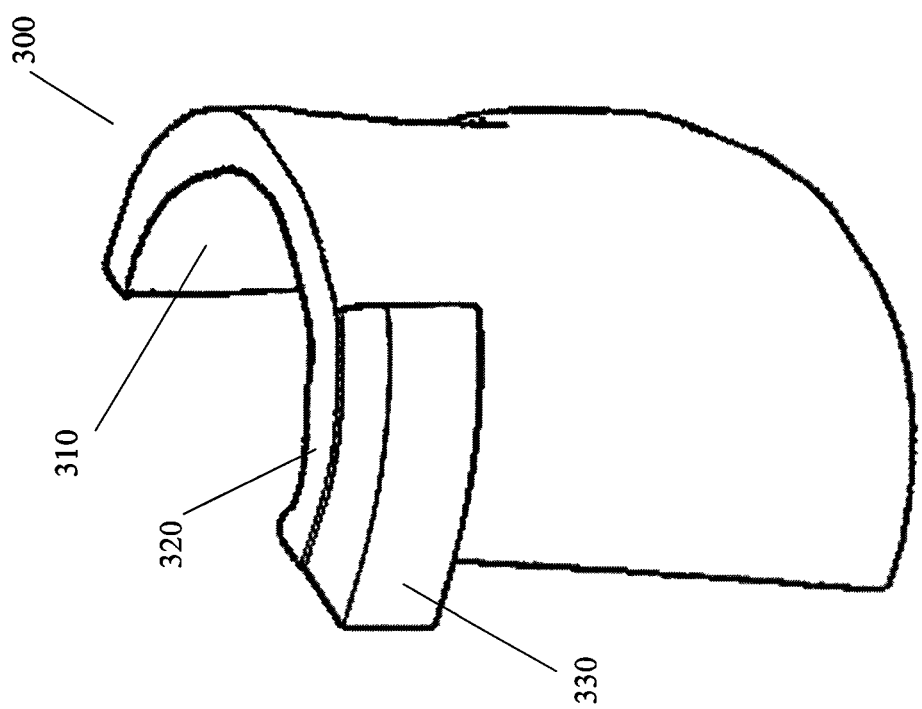
Figure 12:
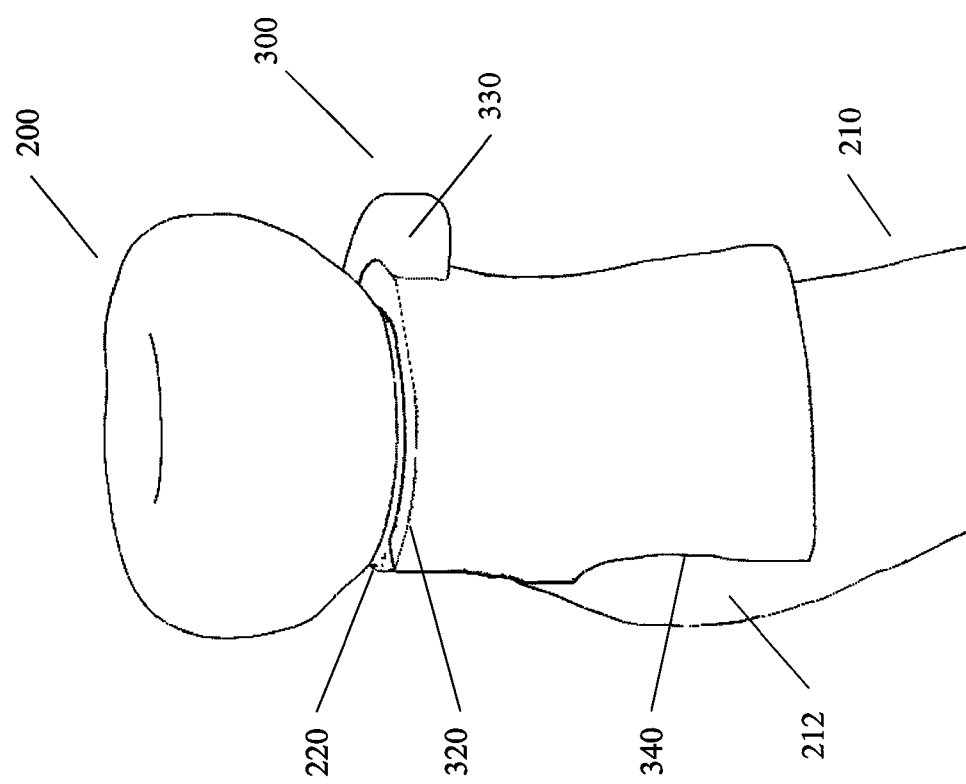
FIG. 12 shows an example of a patient-specific cutting guide, an example of surgical tools fabricated in accordance with the present invention, applied to and interlocking the surface of a small joint bone (radial head) subject to resection.
Figure 13B:
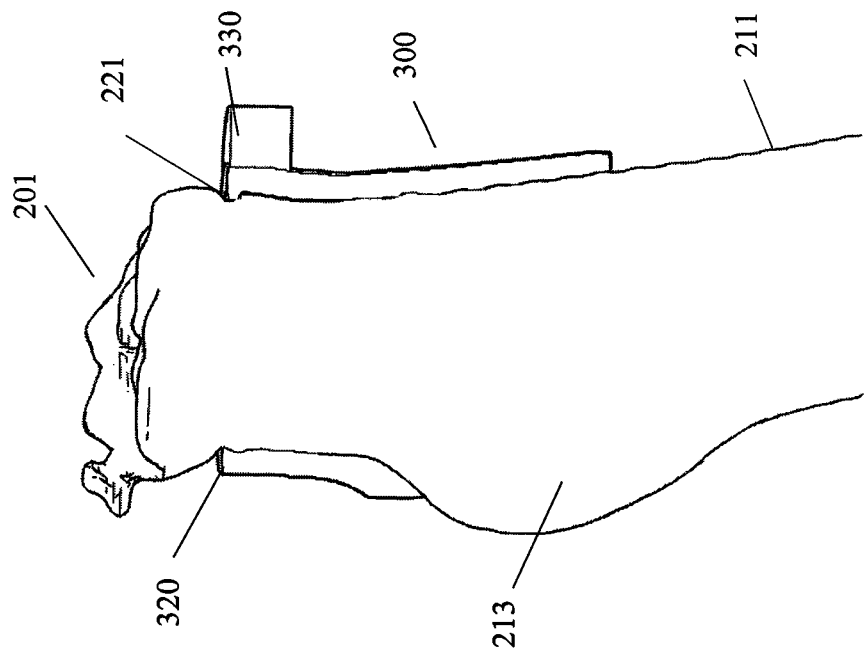
FIGS. 13A and 13B show an example of a patient-specific cutting guide, an example of surgical tools fabricated in accordance with the present invention, applied to and interlocking the surface of a small joint bone (radial head) subject to resection, whereby said bone's head has been substantially deformed or damaged.
Figure 13A:
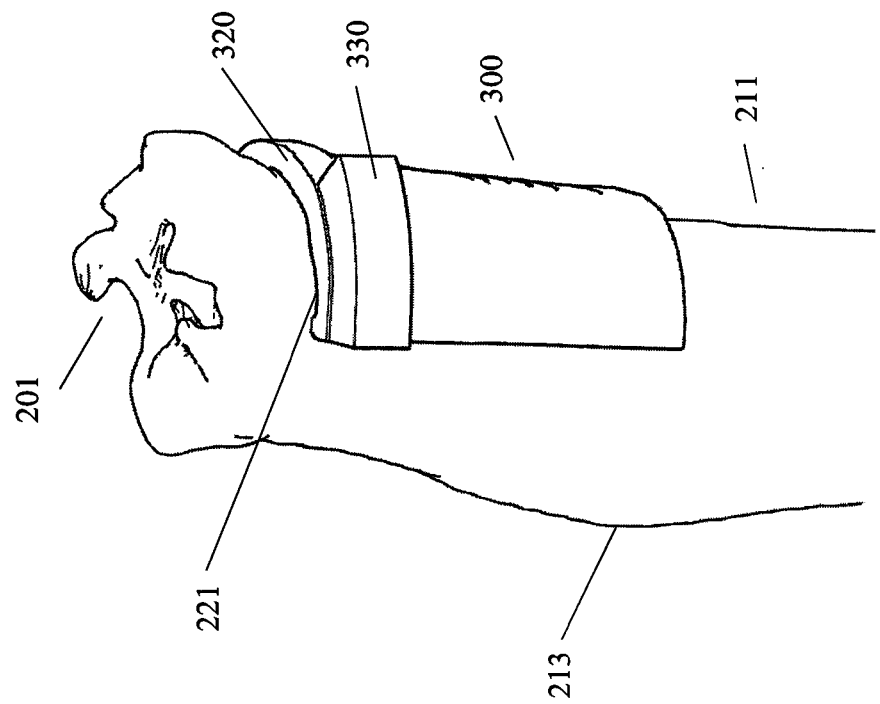

THE SURGICAL TOOL. FIGS. 11A and 11B show a cutting guide 300, one embodiment of a surgical tool that owes its fabrication to the concept of present invention. FIG. 12 shows an application of one embodiment of cutting guide 300 during the resection of defective or pathological radial head 200 from the bone shaft 210, in which a cutting guide 300 is fitted over the bone shaft 210 in the manner that its inner surface 310 is in direct contact with, and effectively interlocking, the cortical surface of a bone shaft 210. The operating surgeon may promptly locate the resection site 220 by an edge 320 of a cutting guide 300. In another embodiment, a cutting guide 300 has a ridge 330 which enables an even more precise guidance for the cutting position and direction. It is also shown on FIGS. 12, 13A and 13B that a cutting guide 300 in accordance with the present invention may be held against and interlock a cortical surface of a bone shaft (210 or 211) and producing an effective friction for purposes of being held still and firmly aid the resection even where a head 200 of bone subject to resection has been missing 201 due to a fracture or decay, as shown in FIGS. 13A and 13B.

THE SURGICAL TOOL. FIGS. 11A and 11B show a cutting guide 300, one embodiment of a surgical tool that owes its fabrication to the concept of present invention. FIG. 12 shows an application of one embodiment of cutting guide 300 during the resection of defective or pathological radial head 200 from the bone shaft 210, in which a cutting guide 300 is fitted over the bone shaft 210 in the manner that its inner surface 310 is in direct contact with, and effectively interlocking, the cortical surface of a bone shaft 210. The operating surgeon may promptly locate the resection site 220 by an edge 320 of a cutting guide 300. In another embodiment, a cutting guide 300 has a ridge 330 which enables an even more precise guidance for the cutting position and direction. It is also shown on FIGS. 12, 13A and 13B that a cutting guide 300 in accordance with the present invention may be held against and interlock a cortical surface of a bone shaft (210 or 211) and producing an effective friction for purposes of being held still and firmly aid the resection even where a head 200 of bone subject to resection has been missing 201 due to a fracture or decay, as shown in FIGS. 13A and 13B.

In an embodiment shown in FIGS. 11A and 11B, the cutting guide 300 has an inner surface 310 having the topography corresponding to the inverse patient-specific anatomical topography of the intended interlocking small joint (radial head) cortical bone surface. Said inverse anatomical topography of the bone provides effective reference points for interlocking the cortical surface of the bone shaft 210 during the operation.

In one embodiment, where the resection site 220 is close to a conspicuous bone protuberance, such as a tuberosity (212 or 213), the cutting guide 300 is tailored to feature a hollow 340 of a size sufficient to accommodate the base of the conspicuous bone protuberance, so that the latter is used as another reference point for an improved interlocking the cutting guide 300 against the bone shaft 210.

The edge 320 of the cutting guide 300 may be configured so that it has a predetermined angle (not shown) to the axis of the bone shaft 210 to accommodate an angled resection. This variation depends on each patient's specific needs, which may arise from the nature of patient's own anatomy, or their pathology.

Figure 14:
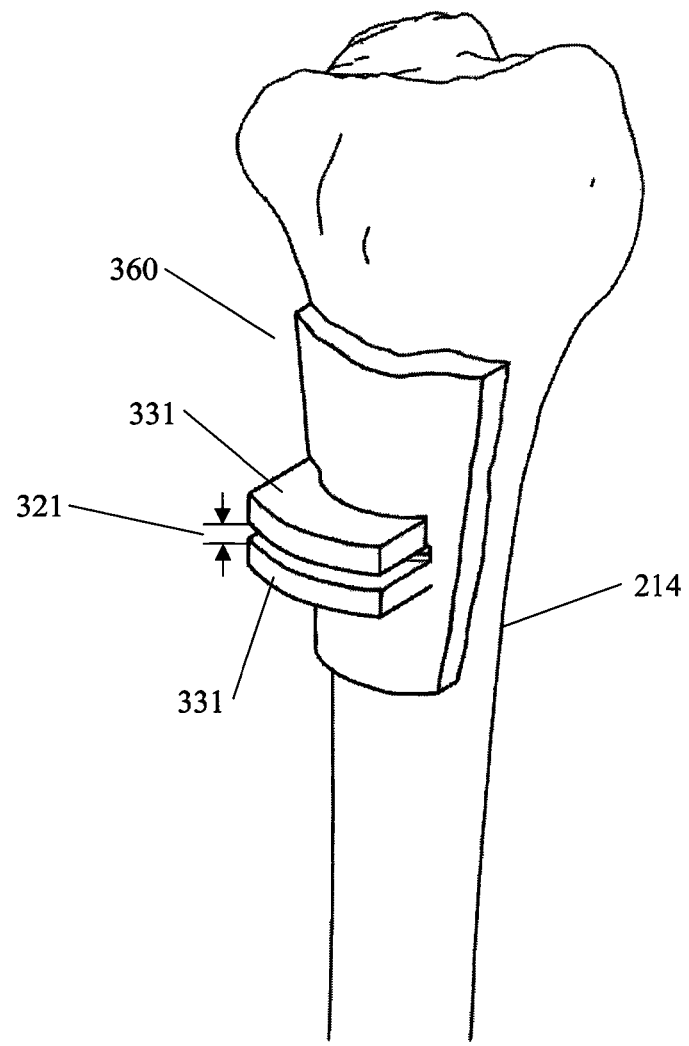
FIG. 14 shows an example of a patient-specific cutting guide, an example of surgical tools fabricated in accordance with the present invention, applied to and interlocking the surface of a small joint bone (distal radius) subject to resection.

In another embodiment as shown in FIG. 14, a cutting guide 360 has an inner surface (not shown) having the topography corresponding to the inverse patient-specific anatomical topography of the intended interlocking small joint (distal radius) cortical bone surface. Said inverse anatomical topography of the bone provides effective reference points for interlocking the cortical surface of the bone shaft 214 during the operation. According to this embodiment, the operating surgeon may promptly locate a resection site (not shown) by a space 321 between double ridges 331 which are approximately parallel to each other.

Figure 15A:
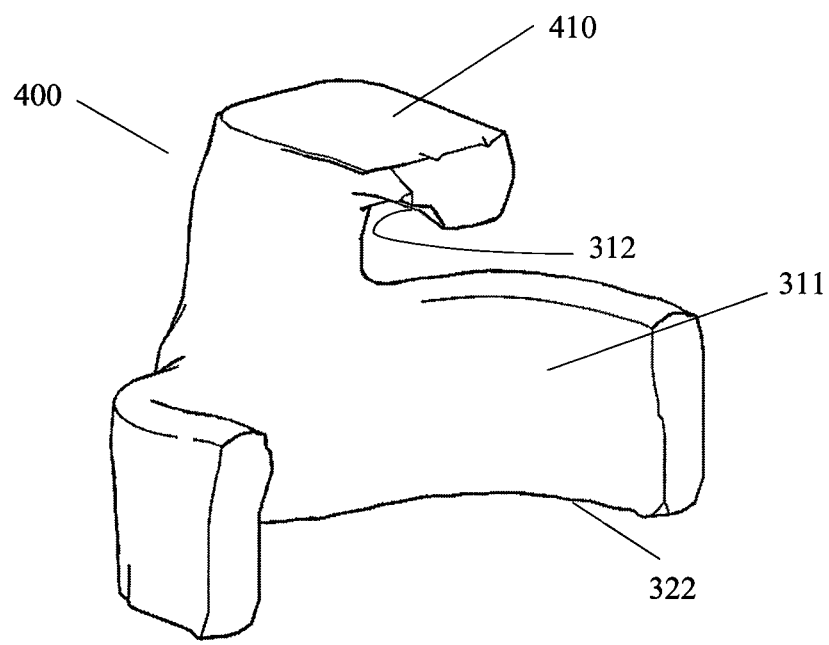
FIGS. 15A and 15B show an example of a patient-specific cutting guide for interphalangeal joint, an example of surgical tools fabricated in accordance with the present invention.
Figure 15B:
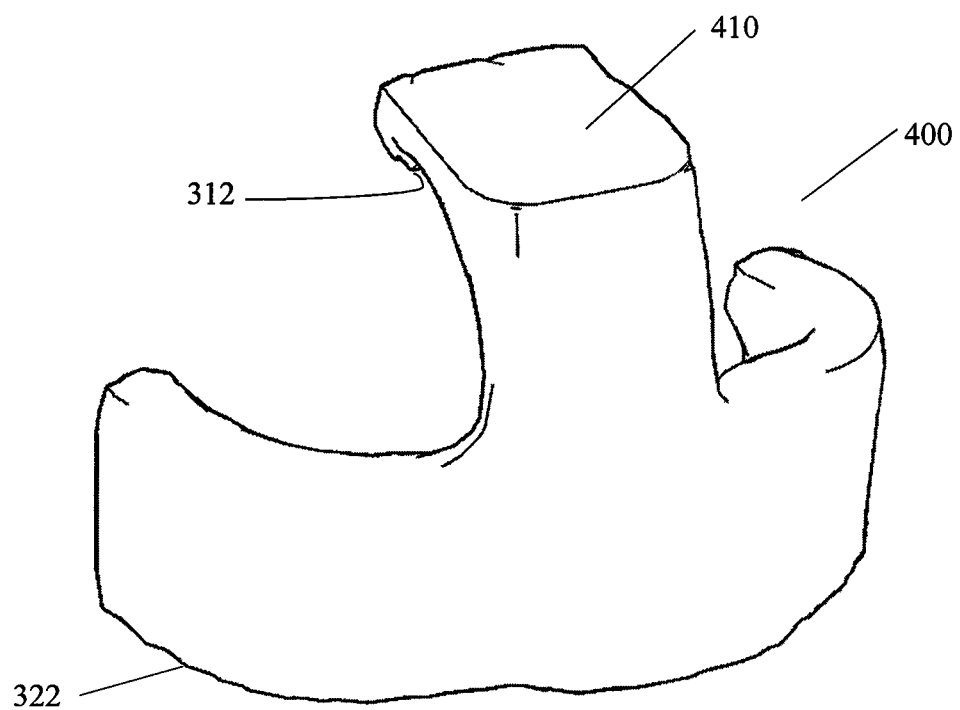

In another embodiment as shown in FIGS. 15A and 15B, a cutting guide 400 has an inner surface 311 having the topography corresponding to the inverse patient-specific anatomical topography of the intended interlocking small joint (interphalangeal joint) cortical bone surface. Said inverse anatomical topography of the bone provides effective reference points for interlocking the cortical surface of the bone shaft (not shown) during the operation. In a preferable embodiment, a resting compartment 410 having patient-specific inner surface 312 provides an additional fit with the patient's anatomy during the operation. According to this embodiment, the operating surgeon may promptly locate a resection site (not shown) by a bottom-end edge 322.

Figure 16A:
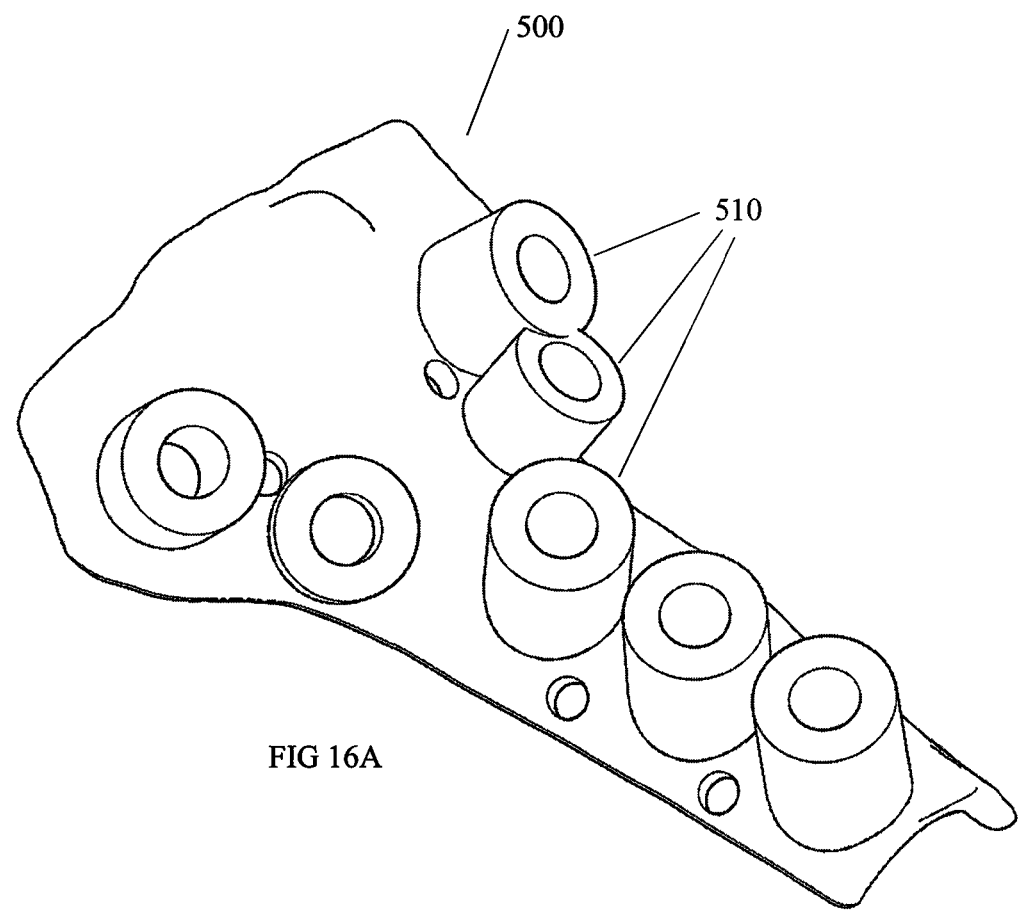
FIGS. 16A and 16B show an example of a patient-specific drilling guide for distal radius, an example of surgical tools fabricated in accordance with the present invention.
Figure 16B:
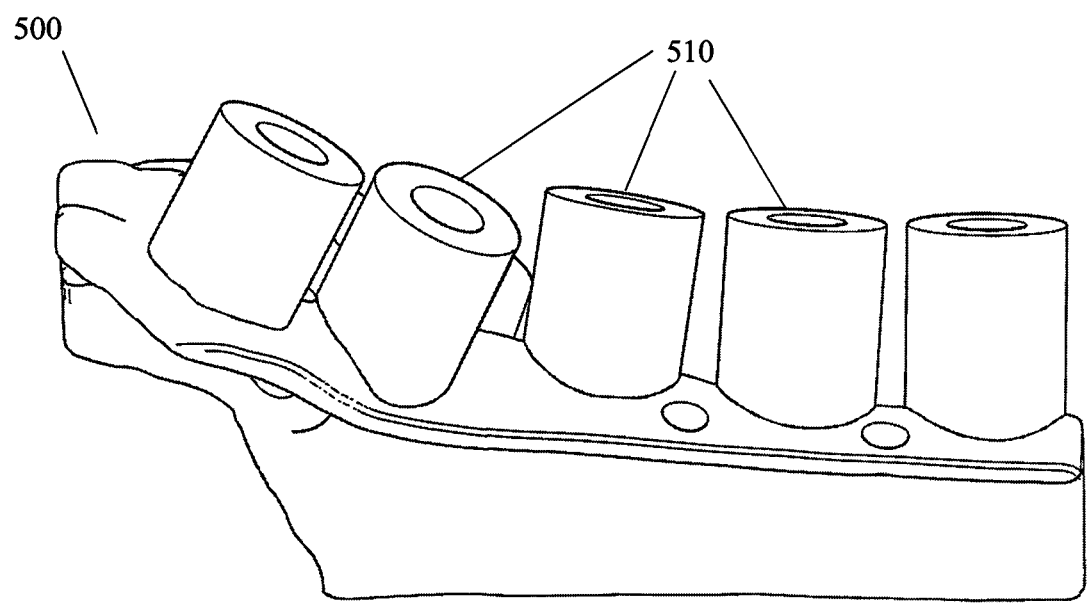

In another exemplary embodiment shown in FIGS. 16A and 16B, the surgical tool is a drilling guide 500. According to this embodiment, an inner surface (not shown) has the topography corresponding to the inverse patient-specific anatomical topography of the intended interlocking small joint (distal radius) cortical bone surface. Said inverse anatomical topography of the bone provides effective reference points for interlocking the cortical surface of the bone shaft (not shown) during the operation. Protruding tubes 510 mark the positions of holes going through the body for precise drilling. These holes also accommodate temporarily fixation by wire(s) (not shown).

Figure 17B:
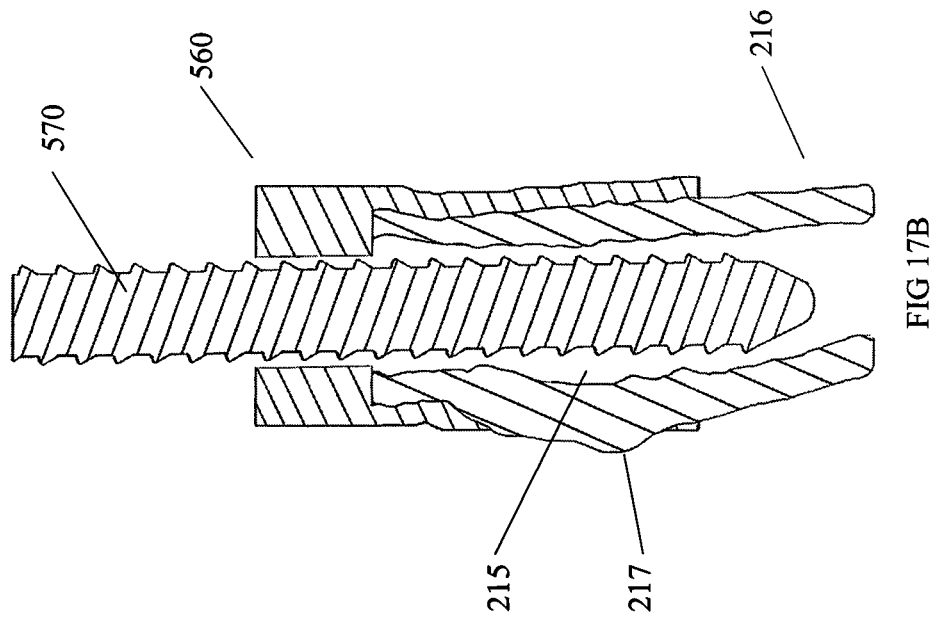
FIGS. 17A and 17B show an example of a patient-specific broaching guide, an example of surgical tools fabricated in accordance with the present invention, applied to and interlocking the surface of a small joint bone (radial head) subject to resection.
Figure 17A:
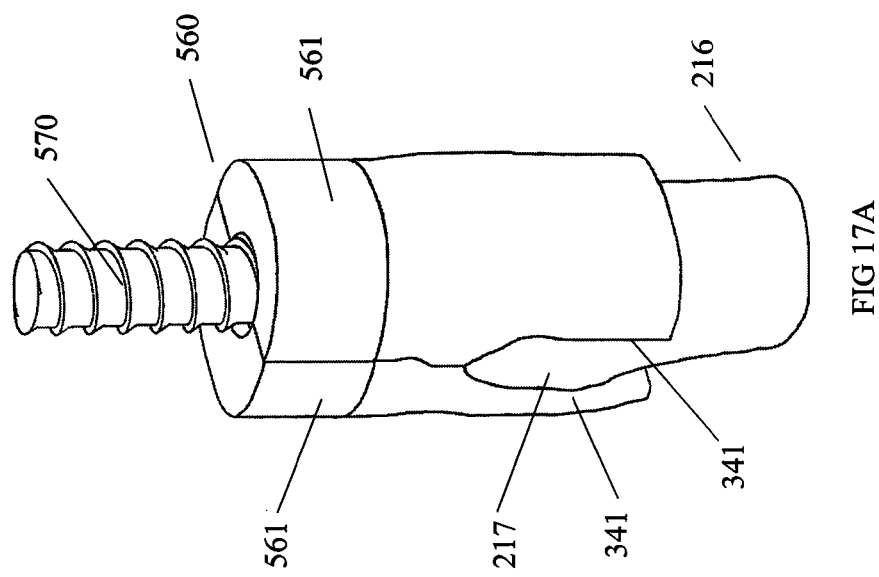

In yet another embodiment as shown in FIGS. 17A and 17B, the surgical tool is broaching guide 560 used for broaching the intramedullary canal 215 to provide an accurate clearance for subsequent insertion of implant. According to this embodiment, the broaching guide 560 has an inner surface (not shown) having the topography corresponding to the inverse patient-specific anatomical topography of the intended interlocking small joint (radial head) cortical bone surface. Said inverse anatomical topography of the bone provides effective reference points for interlocking the cortical surface of the bone shaft 216 during the operation. In a preferred embodiment, the broaching guide 560 has hollow 341 of a size sufficient to accommodate the base of the conspicuous bone protuberance, such as a tuberosity 217, to provide an even better fit with the bone shaft 216. In another preferred embodiment, the broaching guide has two detachable complementary compartments 561. When the two compartments 561 are properly assembled as shown in FIGS. 17A and 17B, a tight, patient-specific fit is achieved. Then a broaching drill 570 is inserted.

The concept in accordance with the present invention may as well be flexibly applied to fabricate surgical tools suitable for different small joint bones. In an exemplary embodiment shown in FIGS. 11A and 11B, the surgical tool (cutting guide 300) is suitable for radial head bone; in another exemplary embodiment shown in FIG. 14, the surgical tool (cutting guide 360) is suitable for distal radius bone; in another exemplary embodiment shown in FIGS. 15A and 15B, the surgical tool (cutting guide 400) is suitable for interphalangeal joint bone. As noted above, the surgical tool may be embodied in forms other than a cutting guide, such as a drilling guide 500 or broaching guide 560. It is further contemplated the concept of the present invention may be applied as effectively to obtain surgical tools for small joint bones located at a shoulder, elbow, wrist, hand, fingers, ankle, foot, or toes.

METHODS FOR IMAGING AND PROCESSING OF THE BONE IMAGE. The process begins with obtaining the anatomic information of relevant bone(s) of each patient from medical images, preferably in three-dimensional. Existing apparatuses that are capable of said imaging include CT-scan and MRI, which are well-understood among the persons skilled in the art.

The most preferable (and in most cases necessary) three-dimensional image is one obtained from the same bone that hosts the resection site. The image of the bone subject to resection will then be diagnosed by accepted medical means to pinpoint the resection site 305, along with the angle of resection, and then to determine on a case-by-case basis whether the same image is good for being used as a fabrication model. If not, then a three-dimensional image of a bone not subject to resection on the opposite side of patient's body is of the second preference.

In the case where the image of the bone not subject to resection is selected, said image is mirrored by techniques known to a person skilled in the art. Preferably, the mirrored image is then processed through a process comprising the steps of registration, morphological measurement, head reconstruction, cartilage compensation, stem design and surgical tool design. These steps may be implemented in more than one possible sequence, and thus the sequence to be disclosed in the following paragraphs are not necessarily chronological. The objective of these steps is to develop the fabrication model which is the closest approximate of the bone subject to resection, using the mirrored image of the bone not subject to resection as a starting basis. Preferably, the reference location for registering the contralateral side (mirrored image) with the bone subject to resection is determined by the area of prominent topography of the bone. In an exemplary embodiment, the area of radial tuberosity combined with 2 cm of proximal diaphysis is selected as a registration reference for designing a radial head prosthesis.

The bone images used in the registration process may be exclusive of their small joint parts, but more preferably inclusive of their small joint parts. In some cases, the injury or deformation occurred to the small joint part of the bone subject to resection may be so severe that it is infeasible to include the images of small joint part into the basis of registration. In such a case, the registration may be carried out based on the bone images exclusive of their respective small joint parts without deviating significantly from the technical effects in accordance with the concept of present invention.

Registration in accordance with this present invention may be based upon either intensity or feature, or both. In the intensity-based registrations, the bone images are aligned with reference to their intensity patterns obtainable from the scanner, e.g. CT-scan and MRI; in the feature-based registrations, the bone images are aligned with reference to their topographic features, e.g. dents, bumps, curvatures, etc. This registration process is preferably carried out automatically with an aid of at least one computer device.

The result of registration process is a transformation matrix whereby the positional data of each 3-D bone image (also known as point cloud data) is transformed into a plurality of transformation matrices having 4×4 dimension. Mathematically, if one data set (e.g. fractured bone) is transformed using the obtained transformation matrix, it will be translated and rotated in such way that it will be finally aligned with the other reference data (e.g. mirror of the healthy bone).

Aligning in accordance with the present invention means aligning the relevant part of the mirrored image of the bone not subject to resection with the relevant part of the bone subject to resection through the transformation matrices. Particularly, said aligning is performed upon a rigid-body basis—that is, only by ways of rotation and geometric translation, but not scaling. Even more particularly, the objective of said alignment is to transform, map, or overlay the two 3-D images in the manner that the volume of common space occupied by both images is maximized, and the volume of space occupied by only either of the two images is minimized. Said objective may be effectively realized by the use of one of several mathematical algorithms known to a person skilled in the art, preferably one which enables interpolation of the values assigned to each voxel selectable from any of known image re-sampling methods, including nearest neighbor, linear interpolation, cubic convolution, and Lanczos algorithm. Subsequent to registration and aligning processes, segmentation methods are applied to extract patient's anatomic information of the relevant bone(s). The results obtained from segmentation process could be in the form of individual points (point-cloud data), surfaces, or solid bodies.

METHODS FOR DESIGNING AND GENERATING THE PATIENT-SPECIFIC IMPLANT AND SURGICAL TOOL. The computer-based method for designing and generating the patient-specific implants composes of five steps. Step A: Measuring morphological parameters. Morphological measurement in accordance with this present invention means "measuring" the anatomical geometry of the to-be-fabricated implant of small joint bone head and/or stem based on point-cloud data. In a preferable embodiment, said point-cloud data are those which have been processed in accordance with the foregoing segmentation step. Said point-cloud data are then subject to a combination of image processing techniques, including and selectable from the search of points and nearest neighbors method, nonlinear least-square method for line and planar fitting, ellipse-fitting method, iterative surface fitting method, principal component analysis and orthogonal projection, or modified methods based on said methods. These techniques are preferably carried out automatically with an aid of at least one computer device. The details of separate enablement for each of said methods are known to a person skilled in the art.

The data obtainable from the morphological measurement includes the parameters defining the size and geometrical characteristics, and variation thereof, of the patient's bone, which will be used for the fabrication of the implant. In an embodiment, the parameters for the small joint bone head obtainable from the morphological measurement are ones defining the head's anatomical contours, including the head diameter, head height, articular depth, dish offsets, and end-plant angles. In another embodiment, the parameters for the small joint bone intramedullary cavity obtainable from the morphological measurement are ones defining the cavity's anatomical clearance, including canal orientation, maximum diameter, minimum diameter and canal length.

Step B: Reconstructing implant's head. Head reconstruction in accordance with this present invention means a step for generating three-dimensional model of implant's head with reference to the available anatomical geometry. The reconstruction may follow the "native" or "anatomical" strategy, depending on the condition of the head of the bone subject to resection. In an exemplary embodiment, where the images of fractured bone head pieces may by reassembled digitally, the "native" reconstruction is adopted, whereby the reassembled image is the basis for an additional correction of the 3D model generated from mirrored bone head image. In another exemplary embodiment, the "anatomical" strategy is adopted, whereby the parameters obtainable from the morphological measurement are the basis for generating three-dimensional model of bone head. In both foregoing exemplary embodiments, the generated bone head image will be further developed towards the final 3-D digital fabrication model.

Step C: Compensating cartilage thickness. Cartilage compensation in accordance with this present invention means a step for additional correction of the bone head image with reference to the thickness of articular cartilage, the dimension of which may not be fully captured by the currently available imaging devices (e.g. a CT scanner) and thus failure to take this thickness into consideration may result in a fabrication of prosthesis bone head which is about 0.5-2.0 mm smaller than the dimension that is effectively patient-specific. In one embodiment, the cartilage compensation is carried out in a uniform fashion whereby the same additional thickness is applied to both the bone head image's fovea and rim. In another embodiment, the cartilage compensation is carried out in a non-uniform fashion whereby the variation of thickness values is applied at different locations of the bone head image. In all the foregoing embodiments, the corrected (i.e. compensated) bone head image will be further developed towards the final 3-D digital fabrication model.

Step D: Generating implant's stem. The stem design in accordance with this present invention means a step for development of the stem part of the fabrication model of bone implant, based on the measured morphological parameters, e.g., intramedullary cavity's orientation and dimensions, and other features which may facilitate the insertion or fitting of the implant stem with the intramedullary cavity, or features that may be preferable or required for each patient's conditions. In an exemplary embodiment, the stem is straight. In another exemplary embodiment, the stem axis follows a customized, patient-specific curve to fit with the patient's anatomical requirements. In yet another exemplary embodiment, the stem surface is configured to have a surface property that prevents rotation or aids the distribution or flow of bone cement, e.g. by a fluted design. In a further exemplary embodiment, the stem has a porous structure or rough surface to promote the bone ingrowth activity. In an even further exemplary embodiment, one or more small holes is created in order to be used for temporary fixation by a wire or screw or a plurality or combination thereof.

The principle similar to the abovementioned stem design may be applied to develop a fabrication model for an orthopedically compatible object, which, despite being intended for insertion into an intramedullary cavity of a small joint bone's shaft, is not intended to be inserted in connection with a prosthesis bone head, and so benefits from the patient-specific morphological parameters of an intramedullary cavity in a similar manner to a prosthetic stem while not being classified as a stem. Examples of said orthopedically compatible objects intended for insertion into an intramedullary cavity of a small joint bone's shaft include a spacer.

Step E: Combining implant's head with stem. The head bone part that has been subject to all necessary and reconstructions and compensations will be combined with the stem part designed in accordance with the foregoing paragraph to form the entire fabrication model for a patient-specific small joint implant.

The surgical tool design in accordance with this present invention means a step for development of the fabrication model for a surgical tool as preferred or required for the resection to be performed. The design will be based on (i) the inverse patient-specific anatomical topography of the small joint bone surface which is obtainable from the aforementioned imaging apparatus and which the surgical tool is intended to interlock during the surgery, (ii) guiding formations having at least one of extension flanges, extension sleeves, bores, holes and pins, and (iii) other functional aspects of the surgical tool which are known by the person skilled in the art (see below examples).

FABRICATION OF THE IMPLANT AND SURGICAL TOOL. After the image of fabrication model has been generated and digitized, a head (e.g. 110, 111, 113, 116, 170) and/or a stem (e.g. 120, 121, 123, 124, 125) and/or an angle 130 and/or the surgical tool (e.g. 300, 360, 400, 500, 560) is fabricated using a 3-D printer, otherwise known as an additive manufacturing machine. The material used in fabrication could be any material recognized as appropriate for the task by a person skilled in the art. Examples of workable materials include those in the family of titanium alloy, cobalt chrome, stainless steel, zirconium alloy, tantalum alloy, polymers or cements. Control and configuration of the 3-D printer depends on the materials used and customization of the part fabricated, which is well within the existing 3-D printing technology.

The dimensions, shape, and topography of a head (e.g. 110, 111, 113, 116, 170) and a surgical tool (e.g. 300, 360, 400, 500, 560) will conform to their respective image used as reference, taking into account the location and angle at a resection site (e.g. 220, 221). It is to be noted that, for the case of a surgical tool, the topography of the bone is inverse to enable an inner surface (e.g. 310, 311) that fits over the cortical surface of bone shaft (e.g. 210, 211, 214, 216).

On the other hand, fabrication of a stem (e.g. 120, 121, 123, 124, 125) and an angle 130 between the head and the stem only needs to refer to the dimensions and shape of the selected image and the location and angle at the resection site—the topography is not relevant here.

In certain embodiments, the stem 120 could be fabricated to be straight as shown in FIG. 5, or curved 121 as shown in FIG. 6. Its surface may also be configured to have a surface property that prevents rotation or aids the distribution or flow of bone cement, in the case that responsible doctor prescribes so. An example of such surface architecture is a fluted surface (e.g. 140, 141, 142).

It is preferable to fabricate all the above implant (e.g. 100, 101, 103, 104, 105) and surgical tool (e.g. 300, 360, 400, 500, 560) to constitute a wholly patient-specific small-joint bone implanting toolkit. However, the fabrication of only part of the toolkit is also possible, as an incomplete toolkit would still offer technical advantage in respect of the part that is made patient specific.

The fabrication process could be broken down into parts, each of which may be carried out in different physical locations and by different entities. This provides flexibility of logistics and fund management. For example, a doctor who runs a personally-owned clinic may choose to collect the images of relevant bone themselves, and then send the images to a third-party 3-D printing service who will fabricate the patient-specific implanting toolkit or part thereof, which will later be delivered to the doctor. This way the doctor is spared of the need to own or maintain a 3-D printer in their own clinic.

Possibly, anyone may choose to take and store images of the relevant bones when they are of fine health, in anticipation of a future possibility where a bone surgery is needed. Alternatively, the present invention may be used to fabricate the toolkit by interpolating the information from an aggregate of digitized bone images obtained from a very large sample size, e.g. national database.

THE INSTALLATION OF IMPLANT. The implanting process begins with determining the resection site (e.g. 220, 221) and angle (not shown) of bone resection to be performed upon a bone shaft (e.g. 210, 211, 214, 216). This step requires a three-dimensional image of bone subject to resection and is carried out in parallel with the fabrication of implant and surgical tool, as explained above.

Next, the surgery technique that is understood by skilled bone surgeon is performed to open the skin, flesh, muscle, tendon, etc., to provide the optimal clearance around the site of operation and expose the small joint bone, which is then cleaned as preparation for the resection. The surgeon may choose any conventional technique that is suitable for each patient's particular case.

After the implant and surgical tool are ready, the cutting guide (e.g. 300, 360, 400) is temporarily fitted over a cortical surface of a bone shaft (e.g. 210, 211, 214, 216) to mark resection site (e.g. 220, 221) with its edge (e.g. 320, 322). The inner surface (e.g. 310, 311), having configured to conform to the inverse topography of the bone, and in some cases featuring a hollow (e.g. 340), will interlock all the reference points (i.e. irregularities including small dents, bumps or even conspicuous protuberance, such as tuberosity 212, 213 or 217), providing a sufficient friction that prevents the cutting guide from sliding laterally over the cortical surface of the bone shaft during the resection, as long as a certain amount of pressure is applied, manually or by an external tool's aid, pushing the cutting guide against the bone shaft. Resection is performed at the resection site, which is located by the edge, using a saw which could be manual or driven by an external power source, at an angle predetermined by the edge. The resection will be completed when the bone head (e.g. 200) has been separated from the bone shaft (e.g. 210).

Subsequently, the intramedullary cavity (e.g. 211, 219) and internal wall (e.g. 218) is cleaned by implementing a broaching guide 560. Then the implant (e.g. 100, 101, 103, 104, 105) is inserted into the intramedullary cavity of the resected bone shaft (e.g. 210, 211, 214, 216). The bottom part of the implant head (e.g. 110, 111, 113, 116, 170) will sit directly upon the resected rim (e.g. 222, 223, 224). In some cases, bone cement is used to aid the adhesion, which is not shown on the Figures.

The wound from the surgery is then sealed by means known to a skilled person, and the patient is sent for further recuperation.

Although the Figures referred above concerns implants, fabrication, and implantation of an elbow's radial head bone, such was meant for exemplifying purposes only. The principle of the present invention equally applies to any small joint of a human body, including shoulder, elbow, wrist, hand, fingers, foot, toes. Applications in relation to said small joints are readily appreciated by a person skilled in the art in light of the above descriptions concerning the radial head alone.

While the present invention has been described with reference to exemplary embodiments, it will be appreciated by those skilled in the art that various changes may be made and equivalence may be substituted for elements thereof without departing from the scope of the present invention. It is to be understood that the present invention is not limited to the particular aspects of the exemplary embodiments disclosed, but it is intended to cover modifications within the spirit and scope of the present invention as disclosed above.

The invention claimed is:

1. A computer-based method of designing a customized patient-specific implant of a small-joint bone, wherein said implant comprises a head and a stem, wherein said small joint bone comprises a shaft and an intramedullary cavity, and wherein said method comprises steps of—
    obtaining a three-dimensional anatomic information of a patient in a form of images, individual points (point-cloud data), surfaces, or solid bodies;
    measuring morphological parameters of the patient's bone;
    identifying anatomic landmarks;
    generating, based on the morphological parameters and anatomic landmarks, a three-dimensional model of the head, wherein said three-dimensional model of the head comprises a contour and a solid body; and
    generating, based on the morphological parameters and anatomic landmarks, a three-dimensional model of the stem, wherein said three-dimensional model of the stem comprises an orthopedically compatible object for insertion into the intramedullary cavity,
    wherein said small joint bone is selectable from a group consisting of elbow, shoulder, wrist, hand, finger, ankle, foot, and toe bones.

2. A computer-based method of claim 1, further comprising a step of compensating a thickness of an articular cartilage, wherein said step further comprises steps of—
    computing a three-dimensional cartilage information of the relevant bone from at least one of a bone database and a patient's CT arthrogram data, wherein said bone database and arthrogram data must be in a form of images, individual points (point-cloud data), surfaces, or solid bodies;
    merging the patient's three-dimensional anatomic information with the referencing three-dimensional cartilage information;
    reconstructing a three-dimensional model of the cartilage, based on the merged information, wherein said three-dimensional model of the cartilage comprises a contour and a solid body; and
    generating a three-dimensional model of the cartilage-compensated head by combining the three-dimensional model of the head with the three-dimensional model of the cartilage.

3. A computer-based method of claim 2, wherein the thickness is non-uniform within a range of about 0.5-2.0 mm.

4. A computer-based method of claim 3, further comprising a step of generating at least a portion of porous structure at least at one of the head and the stem.

5. A computer-based method of claim 2, further comprising a step of generating at least a portion of porous structure at least at one of the head and the stem.

6. A computer-based method of claim 1, further comprising a step of generating at least a portion of porous structure at least at one of the head and the stem.

7. A computer-based method of any of claims 1-4, wherein at least one of the steps of generating a three-dimensional model of the head and generating a three-dimensional model of the stem, is automated and free of human intervention.

8. A computer-based method of claim 7, further comprising a step of fabricating the customized implant by additive manufacturing based on at least one of the three-dimensional model of the head and the three-dimensional model of the stem.

9. A computer-based method of any of claims 1-3, further comprising a step of fabricating the customized implant by additive manufacturing based on at least one of the three-dimensional model of the head and the three-dimensional model of the stem.

10. A customized implant of a small joint bone that is fabricated in accordance with the method of claim 9, said customized implant comprising—
 a head having patient-specific dimensions, shape and topography which correspond to anatomy of said small-joint bone's head;
 a stem for insertion into an intramedullary cavity of said small joint bone's shaft, having patient-specific dimensions and shape which correspond to anatomy of said intramedullary cavity, which is protruding along a longitudinal axis or a curved axis,
 wherein one end of the stem is operatively connected to the head; and
 wherein said small joint bone is selectable from a group consisting of elbow, shoulder, wrist, hand, finger, ankle, foot, and toe bones.

11. A customized implant of claim 10, wherein at least one of the head and the stem has a porous structure.

12. A customized implant of claim 11, wherein the stem is characterized further by being a first stem, wherein the head is characterized further by having a hinged joint attached, and wherein said hinged joint is connected to a second stem.

13. A customized implant of claim 12, wherein the second stem has a porous structure.

14. A customized implant of claim 10, wherein the stem is characterized further by being a first stem, wherein the head is characterized further by having a hinged joint attached, and wherein said hinged joint is connected to a second stem.

15. A customized implant of claim 14, wherein the second stem has a porous structure.

16. A computer-based method of claim 9, wherein fabricating the customized implant by additive manufacturing comprises fabricating:
 the head having patient-specific dimensions, shape and topography which correspond to anatomy of said small-joint bone's head; and
 the stem for insertion into an intramedullary cavity of said small-joint bone's shaft, having patient-specific dimensions and shape which correspond to anatomy of said intramedullary cavity, which is protruding along a longitudinal axis or a curved axis, wherein one end of the stem is operatively connected to the head.

17. A computer-based method of claim 16, wherein fabricating the customized implant includes fabricating at least one of the head and the stem with a porous structure.

18. A computer-based method of claim 16, wherein the stem is a first stem, the head has a hinged joint attached, and wherein fabricating the customized implant includes said hinged joint is connected to a second stem.

19. A computer-based method of claim 18, wherein fabricating the customized implant includes fabricating the second stem with a porous structure.

* * * * *